United States Patent
Lee et al.

(10) Patent No.: US 11,370,735 B2
(45) Date of Patent: Jun. 28, 2022

(54) METHOD FOR DECOMPOSING PHENOLIC BY-PRODUCT

(71) Applicant: LG CHEM, LTD., Seoul (KR)

(72) Inventors: Sang Beom Lee, Daejeon (KR); Min Suk Kang, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/765,104

(22) PCT Filed: Oct. 15, 2019

(86) PCT No.: PCT/KR2019/013513
§ 371 (c)(1),
(2) Date: May 18, 2020

(87) PCT Pub. No.: WO2020/130313
PCT Pub. Date: Jun. 25, 2020

(65) Prior Publication Data
US 2021/0221760 A1    Jul. 22, 2021

(30) Foreign Application Priority Data
Dec. 20, 2018  (KR) .......... 10-2018-0166127

(51) Int. Cl.
*C07C 37/72* (2006.01)
*C07C 37/86* (2006.01)
(Continued)

(52) U.S. Cl.
CPC ............... *C07C 37/72* (2013.01); *C07C 1/20* (2013.01); *C07C 4/24* (2013.01); *C07C 37/52* (2013.01); *C07C 37/86* (2013.01); *C07C 45/82* (2013.01)

(58) Field of Classification Search
CPC .......... C07C 37/72; C07C 37/86; C07C 45/53
See application file for complete search history.

(56) References Cited

U.S. PATENT DOCUMENTS 2,734,085 A * 2/1956 Adams .................... C07C 45/53
568/385
4,262,151 A * 4/1981 Pujado .................... C07C 37/74
568/754
(Continued)

FOREIGN PATENT DOCUMENTS

JP      1996259481 A     10/1996
JP      2004002347 A     1/2004
(Continued)

*Primary Examiner* — Rosalynd A Keys
(74) *Attorney, Agent, or Firm* — Dentons US LLP

(57) ABSTRACT

A method for decomposing a phenolic by-product generated in a phenol preparation process, the method including: adding a phenolic by-product stream, a decomposition apparatus side discharge stream, and process water to a mixing apparatus and mixing the phenolic by-product stream, the decomposition apparatus side discharge stream, and the process water; adding a mixing apparatus discharge stream discharged from the mixing apparatus to a phase separation apparatus and phase-separating the mixing apparatus discharge stream into an oil phase and an aqueous phase; feeding an oil phase stream discharged from the phase-separation apparatus and discharged to a decomposition apparatus and decomposing the oil phase stream; and circulating the decomposition apparatus side discharge stream discharged from the decomposition apparatus to the mixing apparatus.

17 Claims, 4 Drawing Sheets

(51) Int. Cl.
*C07C 4/24* (2006.01)
*C07C 45/82* (2006.01)
*C07C 1/20* (2006.01)
*C07C 37/52* (2006.01)

(56) References Cited

U.S. PATENT DOCUMENTS

| | | | |
|---|---|---|---|
| 5,457,244 A * | 10/1995 | Dyckman | C07C 37/86 |
| | | | 568/754 |
| 5,510,543 A | 4/1996 | Fulmer et al. | |
| 8,530,702 B2 * | 9/2013 | Black | C07C 37/74 |
| | | | 568/324 |
| 9,340,474 B2 | 5/2016 | Kuechler et al. | |
| 2001/0000260 A1 | 4/2001 | Taggart, II et al. | |

FOREIGN PATENT DOCUMENTS

| | | | | |
|---|---|---|---|---|
| JP | 3516168 B2 | 4/2004 | | |
| JP | 2004217529 A | 8/2004 | | |
| JP | 2005029478 A | 2/2005 | | |
| JP | 4337347 B2 * | 9/2009 | | C07C 27/00 |
| JP | 2011-500831 A | 1/2011 | | |
| KR | 10-0262026 B1 | 7/2000 | | |
| KR | 10-20060026476 A | 3/2006 | | |
| KR | 10-20080109764 A | 12/2008 | | |
| KR | 10-20140138325 A | 12/2014 | | |
| KR | 10-2017-0075642 A | 7/2017 | | |

\* cited by examiner

METHOD FOR DECOMPOSING PHENOLIC BY-PRODUCT

CROSS-REFERENCE TO RELATED APPLICATIONS

This application is a U.S. national stage of international Application No. PCT/KR2019/013513, filed on Oct. 15, 2019, and claims the benefit of priority from Korean Patent Application No. 10-2018-0166127, filed on Dec. 20, 2018, the entire contents of which are incorporated herein by reference.

TECHNICAL FIELD

The present invention relates to a method for decomposing a phenolic by-product, and more particularly, to a method for decomposing a phenolic by-product generated in a phenol preparation process.

BACKGROUND

In general, about 95% of phenol used in the world is prepared by a Hock process. The Hock process is performed in three steps including: a step (1) of forming cumene by alkylation of benzene with propylene, a step (2) of oxidizing the cumene to cumene hydroperoxide (CHP) by combining the cumene and oxygen, and a step (3) of decomposing the cumene hydroperoxide into phenol and acetone by an acid decomposition reaction in the presence of an acid catalyst.

Here, in the cumene oxidation step, which is step (2), by-products such as acetophenone (AP), dimethyl benzyl alcohol (DMBA), dicumylperoxide (DCP), and dicumene (DC) are generated in addition to cumene hydroperoxide.

In addition, in the acid decomposition reaction of cumene hydroperoxide in step (3), by-products such as hydroxy acetone (HA), 2-methylbenzofuran (2-MBF), alpha-methyl styrene (AMS), mesityl oxide (MO), alpha-methyl styrene (AMS) dimer, and cumylphenol (CP) are generated in addition to phenol and acetone.

Accordingly, since a product stream generated in such a reaction process is present in a state in which phenol, acetone, and various by-products are mixed, a separation process for separating phenol from the product stream is required.

The product stream is added to a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is added to a phenol column, phenol is separated through a top of the phenol column, and a phenolic by-product such as dicumylperoxide, cumylphenol, alpha-methyl styrene dimer, or tar is separated through a bottom of the phenol column.

Meanwhile, in the related art, the phenolic by-product separated through the bottom of the phenol column was used as fuel or discarded without additional treatment. However, since the phenolic by-product separated through the bottom of the phenol column includes phenol which is a product, some active components such as alpha-methyl styrene, and the like, in addition to tar that is an impurity, the active components are required to be separated and recovered from the phenolic by-product. In addition, in case of decomposing a by-product included in the phenolic by-product, it is possible to prepare cumene and the like.

Accordingly, studies for obtaining phenol and an active component that remain in the phenolic by-product separated through the bottom of the phenol column, and phenol and an active component that are generated by decomposition of the phenolic by-product have been conducted.

SUMMARY

In order to solve the problems mentioned in the background art, an object of the present invention is to prevent a load of a phenol preparation process while obtaining an active component by decomposing a phenolic by-product generated in the phenol preparation process.

That is, an object of the present invention is to provide a method for decomposing a phenolic by-product that is capable of effectively removing a salt contained in the phenolic by-product prior to decomposition of the phenolic by-product and thus preventing a load of a phenol preparation process and an increase in energy consumption, while effectively obtaining an active component by decomposing the phenolic by-product.

In one general aspect, there is provided a method for decomposing a phenolic by-product generated in a phenol preparation process, the method including: a step (S10) of adding a phenolic by-product stream, a decomposition apparatus side discharge stream, and process water to a mixing apparatus and mixing the phenolic by-product stream, the decomposition apparatus side discharge stream, and the process water; a step (S20) of adding a mixing apparatus discharge stream discharged from the mixing apparatus to a phase separation apparatus and phase-separating the mixing apparatus discharge stream into an oil phase and an aqueous phase; a step (S30) of feeding an oil phase stream obtained by the phase-separation in the step (S20) and discharged to a decomposition apparatus and decomposing the oil phase stream; and a step (S40) of circulating the decomposition apparatus side discharge stream obtained by the decomposition in the step (S30) to the mixing apparatus in the step (S10).

According to the method for decomposing a phenolic by-product according to the present invention, in a case where the phenolic by-product generated in the phenol preparation process is decomposed, the salt contained in the phenolic by-product may be effectively removed prior to decomposition of the phenolic by-product, and a content of acetophenone in the active component may be thus reduced, while effectively obtaining an active component by decomposing the phenolic by-product.

In addition, according to the method for decomposing a phenolic by-product according to the present invention, in the case where the phenolic by-product generated in the phenol preparation process is decomposed, a load of the phenol preparation process and an increase in energy consumption may be prevented.

DETAILED DESCRIPTION

Figure 1:
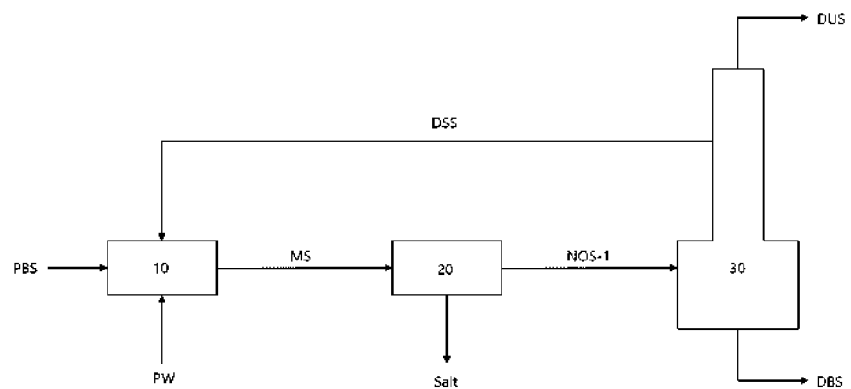
FIG. 1 is a process flowchart illustrating a method for decomposing a phenolic by-product according to an exemplary embodiment of the present invention.

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in the best mode.

In the present invention, the term "stream" may mean a flow of a fluid in a process and may also mean a fluid itself flowing through a pipe. Specifically, the "stream" may mean both a fluid itself flowing through a pipe connecting respective apparatuses and a flow of the fluid. In addition, the fluid may mean gas.

Hereinafter, the present invention will be described in more detail for assisting in understanding of the present invention.

A method for decomposing a phenolic by-product according to the present invention may be a method for decomposing a phenolic by-product generated in a phenol preparation process. According to an exemplary embodiment of the present invention, the phenol preparation process may be a Hock process.

According to an exemplary embodiment of the present invention, the method for decomposing a phenolic by-product may include: a step (S10) of adding a phenolic by-product stream PBS, a decomposition apparatus side discharge stream DSS, and process water PW to a mixing apparatus 10 and mixing the phenolic by-product stream PBS, the decomposition apparatus side discharge stream DSS, and the process water PW; a step (S20) of adding a mixing apparatus discharge stream MS discharged from the mixing apparatus 10 to a phase separation apparatus 20 and phase-separating the mixing apparatus discharge stream MS into an oil phase and an aqueous phase; a step (S30) of feeding an oil phase stream NOS-1 obtained by the phase-separation in the step (S20) and discharged to a decomposition apparatus 30 and decomposing the oil phase stream NOS-1; and a step (S40) of circulating the decomposition apparatus side discharge stream DSS obtained by the decomposition in the step (S30) to the mixing apparatus in the step (S10).

According to an exemplary embodiment of the present invention, the phenol preparation process including an acid decomposition reaction of cumene hydroperoxide described above may be performed. In this case, since the acid decomposition reaction of cumene hydroperoxide is performed while including an acid, an acid decomposition reaction solution contains an acid. Therefore, in order to obtain phenol and acetone from the acid decomposition reaction solution by a process such as distillation, a process of neutralizing the acid decomposition reaction solution is required.

The acid decomposition reaction solution is neutralized by a basic aqueous solution and the like prior to separation of the acid decomposition reaction solution, and in this case, in the neutralized acid decomposition reaction solution, a salt is generated by a neutralization reaction between an acid used in the acid decomposition reaction and a base in the basic aqueous solution. The acid decomposition reaction solution neutralized in the neutralization process is phase-separated into an oil phase and an aqueous phase, and a separation process for obtaining phenol and acetone from the separated oil phase is performed. Here, most of the salt is removed together with the aqueous phase, but a part of the salt remains in the oil phase.

Such a salt finally remains in the phenolic by-product described in the present invention after being subjected to the phenol separation process. The salt remaining in the phenolic by-product causes corrosion, blockage, and deposition in the decomposition apparatus when the phenolic by-product is decomposed in order to obtain an active component from the phenolic by-product later, which causes a failure of the decomposition apparatus. Therefore, when the phenolic by-product is decomposed, it is important to minimize the salt in the phenolic by-product.

Figure 5:
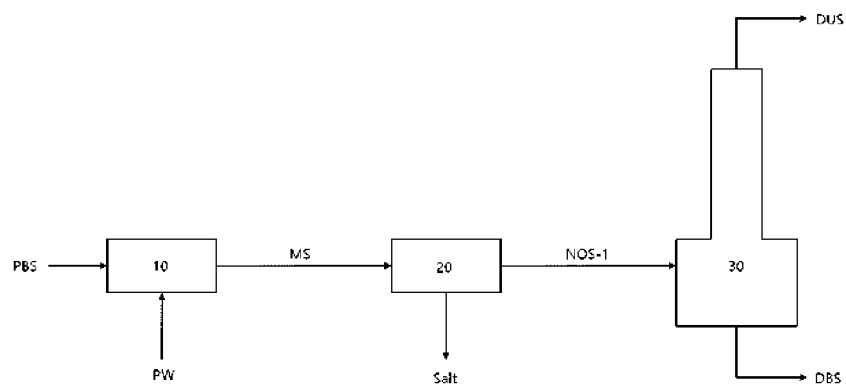
FIG. 5 is a process flowchart illustrating a method for decomposing a phenolic by-product according to Comparative Examples 1 and 2 of the present invention.

Accordingly, as a method of removing a salt in a phenolic by-product, a method of removing a salt by adding process water prior to decomposition of a phenolic by-product may be considered; however, in this case, a phase separation of an oil phase and an aqueous phase is not smoothly performed and thus, the salt may not be sufficiently removed (see FIG. 5).

Figure 6:
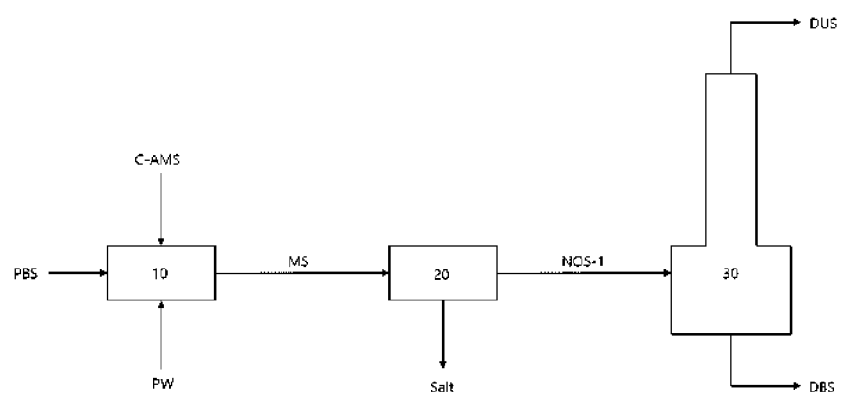
FIG. 6 is a process flowchart illustrating a method for decomposing a phenolic by-product according to Comparative Example 3 of the present invention.

In addition, a method of removing a salt by adding organic substances such as cumene and alpha-methyl styrene discharged, as active components, from an acetone column in a phenol preparation process, to a phenolic by-product together with process water may be considered; however, in this case, since cumene and alpha-methyl styrene are required to be obtained as a product again, an overload occurs in the phenol preparation process and the entire operating energy is increased (see FIG. 6).

Figure 7:
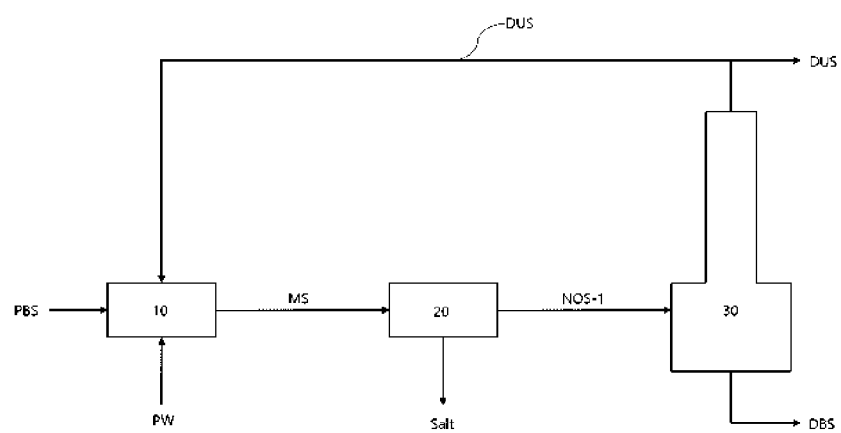
FIG. 7 is a process flowchart illustrating a method for decomposing a phenolic by-product according to Comparative Example 4 of the present invention.

In addition, a method of removing a salt by adding organic substances such as phenol, cumene, and alpha-methyl styrene discharged, as active components, from an upper discharge stream of the decomposition apparatus (30) (that is, DUS) for decomposing a phenolic by-product, to a phenolic by-product together with process water may be considered; however, in this case, since the decomposition apparatus upper discharge stream DUS obtained as an active component is used as it is, a purification efficiency is reduced and a circulated stream is reduced, and thus cold and heat are additionally required to operate a condenser at an upper portion of the decomposition apparatus, which results in an increase in the entire operating energy (see FIG. 7).

On the other hand, according to the method for decomposing a phenolic by-product according to the present invention, a salt in the phenolic by-product may be minimized. Accordingly, the phenolic by-product decomposition apparatus may be stably operated to decompose the phenolic by-product, which is effective in efficiently obtaining an active component.

Hereinafter, the method for decomposing a phenolic by-product according to the present invention will be described in more detail with reference to the drawings.

Referring to FIGS. 1 to 4, the step (S10) is a step for minimizing a salt in the phenolic by-product, and may be a step of adding a phenolic by-product stream PBS, and a decomposition apparatus side discharge stream DSS and process water PW which are to be described below, to the mixing apparatus 10, before the phenolic by-product stream PBS is directly fed to the decomposition apparatus 30 as in the related art, and mixing them.

According to an exemplary embodiment of the present invention, the phenolic by-product stream PBS may contain one or more selected from the group consisting of phenol, alpha-methyl styrene, acetophenone, cumylphenol, and alpha-methyl styrene dimer. As a specific example, the phenolic by-product stream PBS may contain two or more selected from the group consisting of phenol, alpha-methyl styrene, acetophenone, cumylphenol, and alpha-methyl styrene dimer or may contain all of these components. These components may be components included in the phenolic by-product discharged in the process of separating the acetone-based mixture and the phenolic mixture from the acid decomposition reaction solution in the phenol preparation process by the decomposition apparatus and separating phenol and the phenolic by-product from the phenolic mixture by a phenol column.

Meanwhile, according to an exemplary embodiment of the present invention, the decomposition apparatus side discharge stream DSS is a stream discharged through a side of the decomposition apparatus 30 to be described below, and may contain one or more selected from the group consisting of phenol, acetophenone, alpha-methyl styrene, and cumene. As a specific example, the decomposition apparatus side discharge stream DSS may contain phenol, acetophenone, alpha-methyl styrene, and cumene. The reason why the decomposition apparatus side discharge stream DSS is added to the mixing apparatus 10 is to minimize the salt remaining in the oil phase by activating a phase separation of an oil phase and an aqueous phase containing a salt when acetophenone contained in the decomposition apparatus side discharge stream DSS is obtained by the phase-separation in a step (S20) to be described below.

In particular, a content of acetophenone contained in the decomposition apparatus side discharge stream DSS may be 50 wt % or more, 60 wt % or more, or 60 wt % to 99 wt %. The acetophenone is an organic substance originally contained in the phenolic by-product stream PBS and acts as an impurity when using the active component obtained by the phenolic by-product decomposition reaction. Accordingly, it is preferable that a content of acetophenone in the active component is minimized. Therefore, according to the present invention, in a case where the content of acetophenone contained in the decomposition apparatus side discharge stream DSS is 50 wt % or more, 60 wt % or more, or 60 wt % to 99 wt %, acetophenone may be used for removing the salt in the oil phase of the phenolic by-product in the phase separation step (S20), and the content of acetophenone in the active component obtained by the phenolic by-product decomposition reaction may be minimized, which is advantageous in terms of obtaining the active component.

According to an exemplary embodiment of the present invention, the decomposition apparatus side discharge stream DSS may contain the non-separated remaining phenol obtained from the phenol column and a part of phenol obtained by the decomposition of the phenolic by-product (S30). In this regard, since phenol (boiling point: 181.7° C.) and acetophenone (boiling point: 202° C.) have a small difference in boiling point and form an azeotrope, in a case where an operation temperature of the decomposition apparatus 30 is increased to obtain phenol as much as possible from the upper portion of the decomposition apparatus 30, a part of acetophenone may be discharged while being contained in the active component together with phenol.

Accordingly, the method for decomposing a phenolic by-product of the present invention may be performed by intentionally decreasing an operation temperature to be less than the operation temperature needed for obtaining the entire phenol from the upper portion of the decomposition apparatus 30 so as to discharge acetophenone as much as possible through the decomposition apparatus side discharge stream DSS. Therefore, phenol may be contained in the decomposition apparatus side discharge stream DSS. As such, phenol contained in the decomposition apparatus side discharge stream DSS is circulated to the mixing apparatus 10, such that phenol may be continuously recovered from the decomposition apparatus 30 according to the circulation process.

As a specific example, a content of phenol contained in the decomposition apparatus side discharge stream DSS may be 1 wt % to 10 wt %, 1 wt % to 8 wt %, or 1 to 7 wt %. In this range, a content of the salt in the phenolic by-product is minimized and a content of acetophenone in the decomposition apparatus upper discharge stream DUS is minimized.

In addition, according to an exemplary embodiment of the present invention, the process water PW is for removing the salt by dissolving the salt in the phenolic by-product stream PBS, and may refer to water containing various aqueous solutions such as an acidic aqueous solution and a basic aqueous solution, other than distilled water.

According to an exemplary embodiment of the present invention, a pH of the process water PW may be 3.5 to 7, 3.5 to 5.5, or 3.5 to 4.5, and in this range, solubility of salt is improved and a phase separation ability when the phase separation of the oil phase and the aqueous phase is performed in the phase separation apparatus 20 is improved, while preventing corrosion in the mixing apparatus 10 and the phase separation apparatus 20.

In addition, according to an exemplary embodiment of the present invention, the process water PW may include process water PW derived from an aqueous phase solution separated in a step (S20) to be described below (see FIG. 2). As a specific example, the process water PW may be fed from a part of the aqueous phase solution separated in the step (S20). In this case, when the phenolic by-product is decomposed, the process water PW is continuously circulated in the process, such that the amount of process water PW newly added may be minimized.

Meanwhile, according to an exemplary embodiment of the present invention, the mixing apparatus 10 in the step (S10) may be a mixer for mixing the phenolic by-product stream PBS, the decomposition apparatus side discharge stream DSS, and the process water PW. As a specific example, the mixer may be a mixer provided with a line mixer or a static mixer, in order to easily mix the phenolic by-product stream PBS, the decomposition apparatus side discharge stream DSS, and the process water PW.

In addition, according to an exemplary embodiment of the present invention, the phenolic by-product stream PBS and the decomposition apparatus side discharge stream DSS may be added and mixed at a ratio of 1:0.1 to 1, 1:0.2 to 0.5, or 1:0.25 to 0.33 based on a weight or a flow rate, and the phenolic by-product stream PBS and the process water PW may be added and mixed at a ratio of 1:1 to 5, 1:1 to 3, or 1:1.25 to 1.4 based on a weight or a flow rate. In this range, not only the mixing of the phenolic by-product stream PBS, the decomposition apparatus side discharge stream DSS, and the process water PW but also the phase separation ability of the oil phase and the aqueous phase in a step (S20) to be described below are improved, and thus a removal efficiency of salt is improved.

According to an exemplary embodiment of the present invention, the step (S20) may be a step of removing the salt from the mixing apparatus discharge stream MS discharged from the mixing apparatus 10, adding the mixing apparatus discharge stream MS to the phase separation apparatus 20, and phase-separating the mixing apparatus discharge stream MS into an oil phase and an aqueous phase in order to add the mixing apparatus discharge stream MS to the decomposition apparatus 30.

According to an exemplary embodiment of the present invention, the oil phase stream NOS-1 phase-separated and discharged in and from the phase separation apparatus 20 is a stream in which the salt is removed from the phenolic by-product stream PBS in the step (S10) and the step (S20), and the oil phase stream NOS-1 may be used as a feeding stream of the decomposition apparatus 30. The decomposition apparatus 30 using the oil phase stream NOS-1 as a feeding stream is in a state in which a content of the salt in the feeding stream is minimized, such that corrosion, blockage, and deposition in the decomposition apparatus 30 may be prevented when the phenolic by-product is decomposed.

In addition, according to an exemplary embodiment of the present invention, an aqueous phase stream phase-separated and discharged in and from the phase separation apparatus 20 may contain a salt, which effectively removes the salt from the phenolic by-product stream PBS. Meanwhile, as described above, a part of the aqueous phase stream may be re-fed as the process water PW in the step (S10).

According to an exemplary embodiment of the present invention, the phase separation apparatus 20 in the step (S20) may be a drum for phase-separation of an oil phase and an aqueous phase.

According to an exemplary embodiment of the present invention, the step (S20) may include a step of allowing a phase separation solution derived from the mixing apparatus discharge stream MS to remain in the phase separation apparatus 20 for 1 to 10 hours, 2 to 8 hours, or 3 to 5 hours in order for the phase-separation of the oil phase and the aqueous phase. As such, in a case where the phase separation solution is allowed to remain in the phase separation apparatus 20, the phase separation may be more clearly performed, which effectively removes the salt from the aqueous phase as much as possible.

According to an exemplary embodiment of the present invention, the step (S30) may be a step of feeding the oil phase stream NOS-1 phase-separated in the step (S20) and discharged, that is, the phenolic by-product in which the content of the salt is minimized, to the decomposition apparatus 30, and decomposing the oil phase stream NOS-1.

According to an exemplary embodiment of the present invention, the decomposition performed in the decomposition apparatus 30 may be thermal cracking, and the decomposition apparatus 30 for performing the thermal cracking may be a thermal cracker. As a specific example, the thermal cracker may be a reactor-distillation tower integrated type separation apparatus.

According to an exemplary embodiment of the present invention, as described above, the decomposition in the step (S30) may be performed by intentionally decreasing an operation temperature to be less than the operation temperature needed for obtaining the entire phenol from the upper portion of the decomposition apparatus 30 so as to discharge acetophenone as much as possible through the decomposition apparatus side discharge stream DSS.

As a specific example, the decomposition in the step (S30) may be performed at 260° C. to 370° C., 290° C. to 370° C., or 300° C. to 350° C., and in this range, as much acetophenone is discharged as possible through the decomposition apparatus side discharge stream DSS, which effectively minimizes the content of acetophenone in the decomposition apparatus upper discharge stream DUS.

According to an exemplary embodiment of the present invention, the decomposition in the step (S30) may be performed at 0.1 bar to 3.0 bar, 0.1 bar to 2.0 bar, or 0.1 bar to 1.5 bar in order to separate the components of the decomposition apparatus side discharge stream DSS and the decomposition apparatus upper discharge stream DUS. In this case, a low operation temperature of the decomposition apparatus 30 may be maintained, which effectively prevents alpha-methyl styrene of the active component contained in the decomposition apparatus upper discharge stream DUS from being dimerized or polymerized. In addition, the low operation temperature may be maintained, which effectively reduces the thermal energy required during the operation of the decomposition apparatus 30.

In addition, according to an exemplary embodiment of the present invention, the decomposition apparatus 30 may be a multistage decomposition apparatus, and in this case, the decomposition apparatus side discharge stream DSS may be discharged at the middle position (25% to 90%, 40% to 90%, or 50% to 90% of the total stages) of the side of the decomposition apparatus. In this case, it significantly reduces acetophenone discharged through decomposition apparatus upper discharge stream DUS.

According to an exemplary embodiment of the present invention, the decomposition apparatus upper discharge stream DUS obtained by the decomposition in the step (S30) may contain one or more selected from the group consisting of phenol, alpha-methyl styrene, and cumene, as the active component. The active component may contain phenol that is not separated through the bottom of the phenol column and that is contained in the phenolic by-product stream PBS and phenol decomposed in the phenolic by-product decomposition step (S30) and discharged through the decomposition apparatus upper discharge stream DUS. In addition, the active component may contain active components (for example, alpha-methyl styrene, cumene, and the like) that may be used in addition to phenol among components separated through the bottom of the phenol column and contained in the phenolic by-product stream PBS, and active components decomposed in the phenolic by-product decomposition step (S30) and discharged through the decomposition apparatus upper discharge stream DUS. That is, the active component may refer to a component decomposed in the phenolic by-product decomposition step (S30) and discharged through the decomposition apparatus upper discharge stream DUS.

In addition, according to an exemplary embodiment of the present invention, a decomposition apparatus bottom discharge stream DBS discharged by the decomposition in the step (S30) may be recovered as tar and may be reused as fuel and the like.

According to an exemplary embodiment of the present invention, the step (S40) may be a step of circulating the decomposition apparatus side discharge stream DSS obtained by the decomposition in the step (S30) to the mixing apparatus in the step (S10) in order to remove the salt in the phenolic by-product stream PBS. As described above, according to the present invention, in a case where the decomposition apparatus side discharge stream DSS is circulated to the mixing apparatus in the step (S10), the phase separation of the oil phase and the aqueous phase containing the salt is activated during the phase separation in the step (S20), which effectively minimizes the salt remaining in the oil phase.

Figure 3:
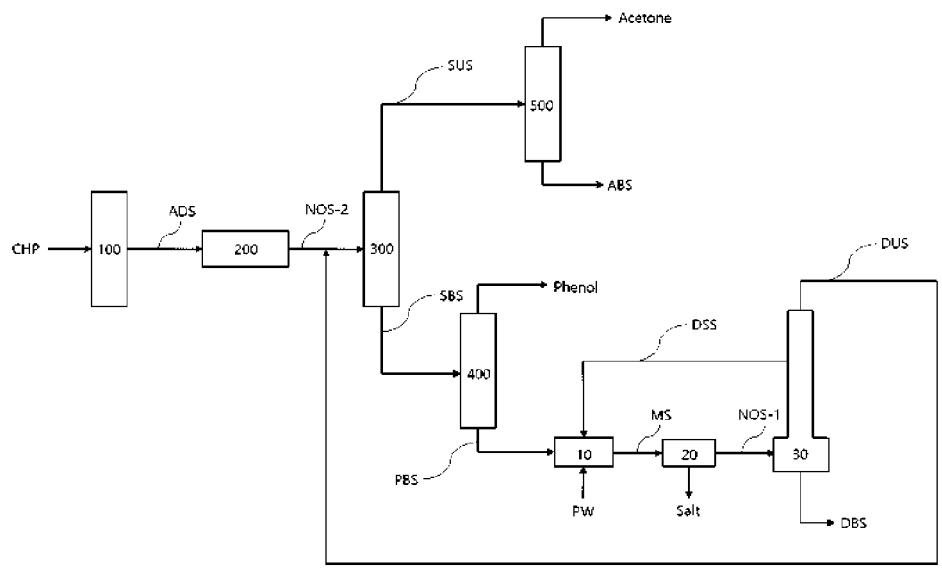
FIG. 3 is a process flowchart illustrating a method for decomposing a phenolic by-product, the method including a phenol preparation process, according to an exemplary embodiment of the present invention.
Figure 4:
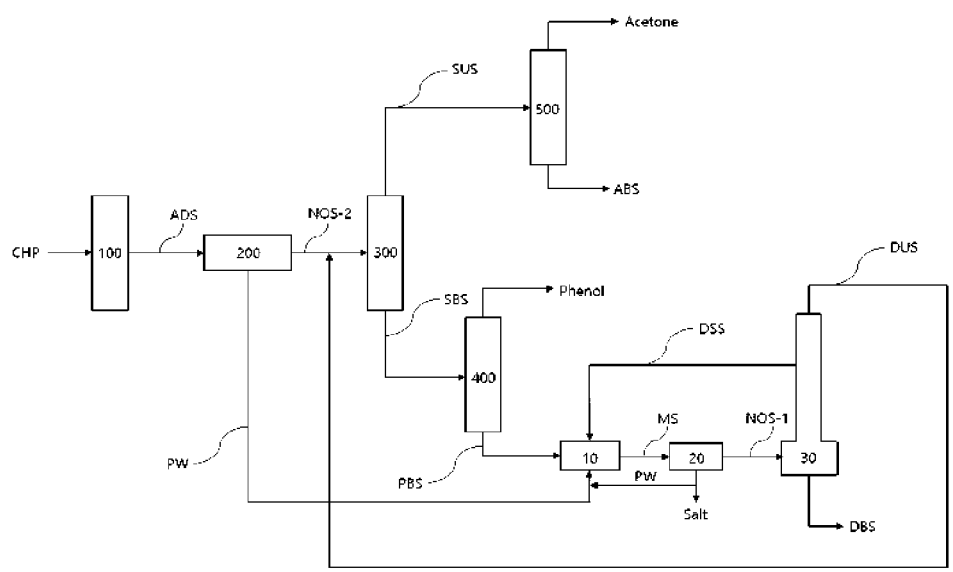
FIG. 4 is a process flowchart illustrating a method for decomposing a phenolic by-product, the method including a phenol preparation process, according to another exemplary embodiment of the present invention.

In addition, a method for decomposing a phenolic by-product according to the present invention may include: as a phenol preparation process, prior to the step (S10), a step (S1) of performing an acid decomposition reaction on cumene hydroperoxide CHP in the presence of an acid catalyst; a step (S2) of adding a basic aqueous solution to an acid decomposition reaction solution ADS discharged in the step (S1), neutralizing the acid decomposition reaction solution ADS, and phase-separating the neutralized acid decomposition reaction solution into an oil phase and an aqueous phase; a step (S3) of adding an oil phase acid decomposition reaction solution separated in the step (S2) to a separation apparatus 300 and separating the oil phase acid decomposition reaction solution into a separation apparatus upper discharge stream SUS containing acetone and a separation apparatus bottom discharge stream SBS containing phenol; and a step (S4) of adding the separation apparatus bottom discharge stream SBS separated in the step (S3) to a phenol column 400 and separating the separation apparatus bottom discharge stream SBS into a phenol column upper discharge stream Phenol containing phenol and a phenol column bottom discharge stream PBS containing a phenolic by-product (see FIGS. 3 and 4).

According to an exemplary embodiment of the present invention, the step (S1) may be a step for preparing an acid decomposition reaction solution containing phenol and acetone by performing an acid decomposition reaction on cumene hydroperoxide CHP in the presence of an acid catalyst. According to an exemplary embodiment of the present invention, the step (S1) may be performed in an acid decomposition reaction apparatus 100 that performs the acid decomposition reaction.

According to an exemplary embodiment of the present invention, the step (S1) may be performed by adding an acid in addition to cumene hydroperoxide CHP, and the acid may be a sulfuric acid.

According to an exemplary embodiment of the present invention, the step (S2) is a step for neutralizing the acid decomposition reaction solution ADS discharged in the step (S1), and may be performed by adding the acid decomposition reaction solution ADS to a neutralization apparatus 200 and adding a basic aqueous solution for neutralizing the acid decomposition reaction solution to the neutralization apparatus 200.

In addition, according to an exemplary embodiment of the present invention, the step (S2) may be a step of separating an oil phase containing phenol and acetone and an aqueous phase containing a salt generated by the neutralization reaction, after the neutralization reaction by the addition of the basic aqueous solution. Here, the separated oil phase may be fed as a feeding stream for separating phenol and acetone, and the aqueous phase may be discharged together with a salt.

Meanwhile, according to an exemplary embodiment of the present invention, the aqueous phase phase-separated and discharged in and from the neutralization apparatus 200 may be re-fed as the process water PW in the step (S10) in order to be used as the process water PW in the step (S10) (see FIG. 4).

That is, according to an exemplary embodiment of the present invention, the process water PW may include process water PW derived from an aqueous phase solution separated in the step (S2) (see FIG. 4). As such, when the phenolic by-product is decomposed, the process water PW is continuously circulated in the phenol preparation process, such that the amount of process water PW newly added may be minimized.

According to an exemplary embodiment of the present invention, the step (S3) may be a step for separating phenol and acetone from an oil phase acid decomposition reaction solution NOS-2 separated in the step (S2). As a specific example, the step (S3) may be performed by including a step of adding the oil phase acid decomposition reaction solution separated in the step (S2) to the separation apparatus 300 and separating the oil phase acid decomposition reaction solution into the separation apparatus upper discharge stream SUS containing acetone and the separation apparatus bottom discharge stream SBS containing phenol.

According to an exemplary embodiment of the present invention, the separation apparatus upper discharge stream SUS separated in the step (S3) may contain acetone and one or more selected from the group consisting of unreacted cumene, acetone, alpha-methyl styrene, and hydroxy acetone. The separation apparatus upper discharge stream SUS may be added to an acetone column 500 in order to obtain acetone, and may be separated into an acetone column upper discharge stream Acetone containing acetone and an acetone column bottom discharge stream ABS containing one or more selected from the group consisting of cumene, alpha-methyl styrene, and hydroxy acetone, at the acetone column 500.

In addition, according to an exemplary embodiment of the present invention, the step (S4) may be a step of adding the separation apparatus bottom discharge stream SBS to the phenol column 400 and separating the separation apparatus bottom discharge stream SBS into the phenol column upper discharge stream Phenol containing phenol and the phenol column bottom discharge stream PBS containing a phenolic by-product, in order to obtain phenol from the separation apparatus bottom discharge stream SBS separated in the step (S3) and decompose the phenolic by-product.

According to an exemplary embodiment of the present invention, the phenol column upper discharge stream Phenol containing phenol may be obtained as a phenol product, and the phenol column bottom discharge stream PBS may be fed to the phenolic by-product stream PBS in the step (S10) in order to decompose the phenolic by-product. That is, the phenolic by-product stream PBS in the step (S10) may be the phenol column bottom discharge stream PBS separated in the step (S4).

According to an exemplary embodiment of the present invention, the decomposition apparatus upper discharge stream DUS obtained by the decomposition in the step (S30) may be mixed with the oil phase acid decomposition reaction solution before the oil phase acid decomposition reaction solution separated in the step (S2) is added to the separation apparatus (see FIG. 4). In this case, phenol of the active component contained in the decomposition apparatus upper discharge stream DUS may be obtained from the phenol column 400 through the phenol column upper discharge stream Phenol as a phenol product after being subjected to the phenol preparation process again, and the one or more selected from the group consisting of cumene and alpha-methyl styrene may be obtained as an acetone column bottom discharge stream ABS at the acetone column 500 through the separation apparatus upper discharge stream SUS after being subjected to the phenol preparation process again.

Hereinafter, the present invention will be described in more detail by means of the following Examples. However, the following Examples are provided for illustrating the present invention. It would be apparent to a person skilled in the art that various modifications and alterations may be made without departing from the scope and spirit of the present invention, and the scope of the present invention is not limited thereto.

EXPERIMENTAL EXAMPLES

Examples 1 and 2

Figure 2:
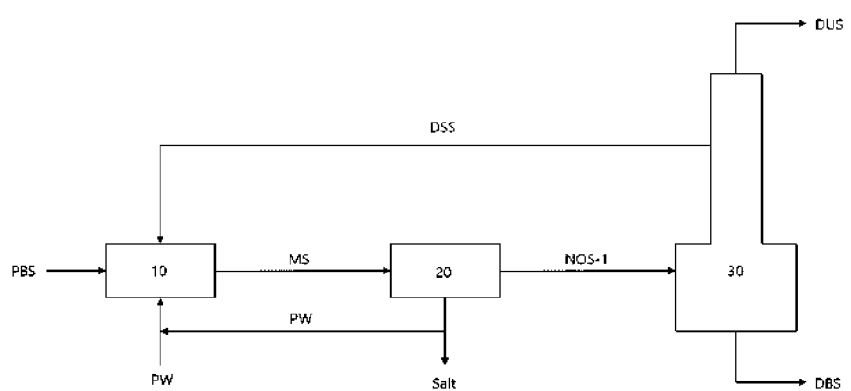
FIG. 2 is a process flowchart illustrating a method for decomposing a phenolic by-product according to another exemplary embodiment of the present invention.

By using the process flowchart illustrated in FIG. 2, a phenolic by-product stream PBS and a decomposition apparatus side discharge stream DSS that have compositions shown in Table 1 were fed to a mixing apparatus 10, and process water PW was fed to the mixing apparatus 10 while maintaining a pH of 4.

A flow rate ratio of the phenolic by-product stream PBS, the decomposition apparatus side discharge stream DSS, and the process water PW added to the mixing apparatus 10 was 1:0.33:1.43 in Example 1 and 1:0.25:1.25 in Example 2, based on 1,000 kg/hr of the phenolic by-product stream PBS.

Thereafter, the mixture was left in the phase separation apparatus 20 of Examples 1 and 2 for 0 hours, 3 hours, and 5 hours, and then a content of a salt in an oil phase subjected to a phase separation and a removal efficiency of a salt were measured. The results are shown in Table 2. In addition, the compositions of the decomposition apparatus upper discharge stream decomposed and discharged according to Examples 1 and 2 are shown in Table 3.

TABLE 1

| Classification | | Phenolic by-product stream PBS | Decomposition apparatus side discharge stream DSS | |
|---|---|---|---|---|
| | | | Example 1 | Example 2 |
| Phenol | (wt %) | 4.99 | 22.41 | 25.29 |
| Alpha-methyl styrene | (wt %) | 5.67 | 6.55 | 8.02 |
| Cumene | (wt %) | 0.00 | 2.07 | 2.50 |
| Acetophenone | (wt %) | 15.45 | 68.96 | 60.57 |
| Cumylphenol | (wt %) | 21.27 | 0.00 | 0.51 |
| Alpha-methyl styrene dimer | (wt %) | 14.00 | 0.00 | 0.48 |
| Others | (wt %) | 38.62 | 0.01 | 2.63 |
| Total | (wt %) | 100.00 | 100.00 | 100.00 |

TABLE 2

| Classification | | Example 1 | Example 2 |
|---|---|---|---|
| PBS:DSS:PW flow rate ratio | | 1:0.33:1.43 | 1:0.25:1.25 |
| Content of salt in oil phase after being left in phase separation apparatus 20 for 0 hours | (ppm) | 400 | 530 |
| Content of salt in oil phase after being left in phase separation apparatus 20 for 3 hours | (ppm) | 25 | 35 |
| Removal efficiency of salt in oil phase after being left in phase separation apparatus 20 for 3 hours | (%) | 94 | 93 |
| Content of salt in oil phase after being left in phase separation apparatus 20 for 5 hours | (ppm) | 25 | 35 |
| Removal efficiency of salt in oil phase after being left in phase separation apparatus 20 for 5 hours | (%) | 94 | 93 |
| Thermal energy increased compared to PBS ton | (Mcal/ton) | 47.5 | 30 |

TABLE 3

| Classification | | Example 1 | Example 2 |
|---|---|---|---|
| Phenol | (wt %) | 23.99 | 21.73 |
| Alpha-methyl styrene | (wt %) | 43.32 | 49.21 |
| Cumene | (wt %) | 20.47 | 23.57 |
| Acetophenone | (wt %) | 7.65 | 0.00 |
| Cumylphenol | (wt %) | 0.00 | 0.00 |
| Alpha-methyl styrene dimer | (wt %) | 0.00 | 0.00 |
| Others | (wt %) | 4.57 | 5.49 |
| Total | (wt %) | 100.00 | 100.00 |

Comparative Examples 1 and 2

By using the process flowchart illustrated in FIG. 5, a phenolic by-product stream PBS having compositions shown in Table 4 was fed to a mixing apparatus 10, and process water PW was fed to the mixing apparatus 10 while maintaining a pH of 4.

In Comparative Examples 1 and 2, a flow rate ratio of the phenolic by-product stream PBS and the process water PW added to the mixing apparatus 10 was 1:1 based on 1,000 kg/hr of the phenolic by-product stream PBS.

Thereafter, the mixture was left in the phase separation apparatus 20 of Comparative Examples 1 and 2 for 0 hours, 3 hours, and 5 hours, and then a content of a salt in an oil phase subjected to a phase separation and a removal efficiency of a salt were measured. The results are shown in Table 5.

TABLE 4

| Classification | | Phenolic by-product stream PBS |
|---|---|---|
| Phenol | (wt %) | 4.99 |
| Alpha-methyl styrene | (wt %) | 5.67 |
| Cumene | (wt %) | 0.00 |

TABLE 4-continued

| Classification | | Phenolic by-product stream PBS |
|---|---|---|
| Acetophenone | (wt %) | 15.45 |
| Cumylphenol | (wt %) | 21.27 |
| Alpha-methyl styrene dimer | (wt %) | 14.00 |
| Others | (wt %) | 38.62 |
| Total | (wt %) | 100.00 |

TABLE 5

| Classification | | Comparative Example | |
|---|---|---|---|
| | | 1 | 2 |
| PBS:PW flow rate ratio | | 1:1 | 1:1 |
| Content of salt in oil phase after being left in phase separation apparatus 20 for 0 hours | (ppm) | 500 | 530 |
| Content of salt in oil phase after being left in phase separation apparatus 20 for 3 hours | (ppm) | 170 | 150 |
| Removal efficiency of salt in oil phase after being left in phase separation apparatus 20 for 3 hours | (%) | 66 | 72 |
| Content of salt in oil phase after being left in phase separation apparatus 20 for 5 hours | (ppm) | 152 | 120 |
| Removal efficiency of salt in oil phase after being left in phase separation apparatus 20 for 5 hours | (%) | 70 | 77 |

Comparative Examples 3 and 4

By using the process flowcharts illustrated in FIGS. 6 and 7 (Comparative Example 3: FIG. 6, Comparative Example 4: FIG. 7), a phenolic by-product stream PBS and crude alpha-methyl styrene (C-AMS) that have compositions shown in Table 6 were fed to a mixing apparatus 10 in Comparative Example 3, a phenolic by-product stream PBS and a decomposition apparatus upper discharge stream DUS that have compositions shown in Table 6 were fed to a mixing apparatus 10, and process water PW was fed to the mixing apparatus 10 while maintaining a pH of 4, in Comparative Example 4.

In Comparative Example 3, a flow rate ratio of the phenolic by-product stream PBS, the C-AMS, and the process water PW added to the mixing apparatus 10 was 1:0.33:1.43 based on 1,000 kg/hr of the phenolic by-product stream PBS. In Comparative Example 4, a flow rate ratio of the phenolic by-product stream PBS, the decomposition apparatus upper discharge stream DUS, and the process water PW added to the mixing apparatus 10 was 1:0.33:1.43 based on 1,000 kg/hr of the phenolic by-product stream PBS.

Thereafter, the mixture was left in the phase separation apparatus 20 of Comparative Examples 3 and 4 for 0 hours, 3 hours, and 5 hours, and then a content of a salt in an oil phase subjected to a phase separation and a removal efficiency of a salt were measured. The results are shown in Table 7. In addition, the compositions of the decomposition apparatus upper discharge stream decomposed and discharged according to Comparative Examples 3 and 4 are shown in Table 8.

TABLE 6

| Classification | | Phenolic by-product stream PBS | C-AMS | Decomposition apparatus upper discharge stream DUS |
|---|---|---|---|---|
| Phenol | (wt %) | 4.99 | 0.00 | 24.21 |
| Alpha-methyl styrene | (wt %) | 5.67 | 20.00 | 41.92 |
| Cumene | (wt %) | 0.00 | 80.00 | 21.66 |
| Acetophenone | (wt %) | 15.45 | 0.00 | 7.63 |
| Cumylphenol | (wt %) | 21.27 | 0.00 | 0.00 |
| Alpha-methyl styrene dimer | (wt %) | 14.00 | 0.00 | 0.00 |
| Others | (wt %) | 38.62 | 0.00 | 4.58 |
| Total | (wt %) | 100.00 | 100.00 | 100.00 |

TABLE 7

| Classification | | Comparative Example | |
|---|---|---|---|
| | | 3 | 4 |
| PBS:(C-AMS or DUS):PW flow rate ratio | | 1:0.33:1.43 | 1:0.33:1.43 |
| Content of salt in oil phase after being left in phase separation apparatus 20 for 0 hours | (ppm) | 500 | 400 |
| Content of salt in oil phase after being left in phase separation apparatus 20 for 3 hours | (ppm) | 40 | 70 |
| Removal efficiency of salt in oil phase after being left in phase separation apparatus 20 for 3 hours | (%) | 92 | 83 |
| Content of salt in oil phase after being left in phase separation apparatus 20 for 5 hours | (ppm) | 20 | 20 |
| Removal efficiency of salt in oil phase after being left in phase separation apparatus 20 for 5 hours | (%) | 96 | 77 |
| Thermal energy increased compared to PBS ton | (Mcal/ton) | 90 | 154 |

TABLE 8

| Classification | | Comparative Example | |
|---|---|---|---|
| | | 3 | 4 |
| Phenol | (wt %) | 14.70 | 24.21 |
| Alpha-methyl styrene | (wt %) | 33.23 | 41.92 |

TABLE 8-continued

| | | Comparative Example | |
|---|---|---|---|
| Classification | | 3 | 4 |
| Cumene | (wt %) | 45.35 | 21.66 |
| Acetophenone | (wt %) | 4.13 | 7.63 |
| Cumylphenol | (wt %) | 0.00 | 0.00 |
| Alpha-methyl styrene dimer | (wt %) | 0.00 | 0.00 |
| Others | (wt %) | 2.59 | 4.58 |
| Total | (wt %) | 100.00 | 100.00 |

Referring to Tables 2 and 3, it could be confirmed that the phenolic by-product is decomposed by the method for decomposing a phenolic by-product according to the present invention, such that a large amount of active components was obtained while maintaining a high removal efficiency of the salt contained in the phenolic by-product. Also, it could be confirmed that the consumption of thermal energy was low.

Meanwhile, referring to Table 5, it could be confirmed that in Comparative Examples 1 and 2 in which only the process water PW was added prior to decomposition of the phenolic by-product, the content of the salt was high and the removal efficiency of the salt was significantly reduced even after the phase separation, as compared to those of the present invention.

In addition, referring to Table 7, in Comparative Examples 3 and 4 in which the salt was removed by adding the organic substances such as phenol, cumene, and alpha-methyl styrene to the phenolic by-product together with the process water, the removal efficiency of the salt was quite high, but the consumption of thermal energy was very high as compared to that of the present invention.

From the results as described above, the inventors of the present invention found that in a case where the phenolic by-product generated in the phenol preparation process is decomposed according to the present invention, the content of acetophenone in the active component may be reduced, while efficiently removing the salt contained in the phenolic by-product prior to decomposition of the phenolic by-product and efficiently obtaining the active component by decomposing the phenolic by-product.

The invention claimed is:

1. A method for decomposing a phenolic by-product generated in a phenol preparation process, the method comprising:
   adding a phenolic by-product stream, a decomposition apparatus side discharge stream, and process water to a mixing apparatus and mixing the phenolic by-product stream, the decomposition apparatus side discharge stream, and the process water;
   adding a mixing apparatus discharge stream discharged from the mixing apparatus to a phase separation apparatus and phase-separating the mixing apparatus discharge stream into an oil phase and an aqueous phase;
   feeding an oil phase stream discharged from the phase-separation apparatus to a decomposition apparatus and decomposing the oil phase stream; and
   circulating the decomposition apparatus side discharge stream discharged from the decomposition apparatus to the mixing apparatus.

2. The method of claim 1, wherein the phenolic by-product stream comprises one or more selected from the group consisting of phenol, alpha-methyl styrene, acetophenone, cumylphenol, and alpha-methyl styrene dimer.

3. The method of claim 1, wherein the decomposition apparatus side discharge stream comprises one or more selected from the group consisting of phenol, acetophenone, alpha-methyl styrene, and cumene.

4. The method of claim 1, wherein the decomposition apparatus side discharge stream comprises 50 wt % or more of acetophenone.

5. The method of claim 1, wherein a pH of the process water is 3.5 to 7.

6. The method of claim 1, wherein the process water includes process water derived from the aqueous phase solution.

7. The method of claim 1, wherein a decomposition apparatus upper discharge stream discharged from the decomposition apparatus contains one or more selected from the group consisting of phenol, alpha-methyl styrene, and cumene.

8. The method of claim 1, further comprising:
   prior to adding the phenolic by-product stream,
   performing an acid decomposition reaction on cumene hydroperoxide in the presence of an acid catalyst;
   adding a basic aqueous solution to an acid decomposition reaction solution discharged from the acid decomposition reaction neutralizing the acid decomposition reaction solution, and phase-separating the neutralized acid decomposition reaction solution into an oil phase and an aqueous phase;
   feeding an oil phase acid decomposition reaction solution to a separation apparatus and separating the oil phase acid decomposition reaction solution into a separation apparatus upper discharge stream containing acetone and a separation apparatus bottom discharge stream containing phenol; and
   feeding the separation apparatus bottom discharge stream discharged from the separation apparatus to a phenol column and separating the separation apparatus bottom discharge stream into a phenol column upper discharge stream containing phenol and a phenol column bottom discharge stream containing a phenolic by-product.

9. The method of claim 8, wherein the process water includes process water derived from the aqueous phase.

10. The method of claim 8, wherein the phenolic by-product stream is the phenol column bottom discharge stream.

11. The method of claim 8, wherein a decomposition apparatus upper discharge stream discharged from the decomposition apparatus is mixed with the oil phase before the oil phase is added to the separation apparatus.

12. The method of claim 1, wherein the phenolic by-product stream and the decomposition apparatus side discharge stream are added to the mixing apparatus at a ratio of 1:0.1 to 1:1 based on a weight or a flow rate.

13. The method of claim 12, wherein the phenolic by-product stream and the decomposition apparatus side discharge stream are added to the mixing apparatus at a ratio of 1:0.2 to 1:0.5.

14. The method of claim 13, wherein the phenolic by-product stream and the decomposition apparatus side discharge stream are added to the mixing apparatus at a ratio of 1:0.25 to 1:0.33.

15. The method of claim 1, wherein the phenolic by-product stream and the process water are added to the mixing apparatus at a ratio of 1:1 to 1:5 based on a weight or flow rate.

16. The method of claim 15, wherein the phenolic by-product stream and the process water are added to the mixing apparatus at a ratio of 1:1 to 1:3.

17. The method of claim 16, wherein the phenolic by-product stream and the process water are added to the mixing apparatus at a ratio of 1:1.25 to 1:1.4.

\* \* \* \* \*